United States Patent [19]

Müller et al.

[11] Patent Number: 6,140,048
[45] Date of Patent: Oct. 31, 2000

[54] SYSTEM FOR DISTINGUISHING FLUORESCENT MOLECULE GROUPS BY TIME RESOLVED FLUORESCENCE MEASUREMENT

[75] Inventors: Ralph Müller, Buchen; Markus Sauer, Heidelberg; Christoph Zander, Freudenberg, all of Germany

[73] Assignee: Roche Diagnostics GmbH, Mannheim, Germany

[21] Appl. No.: 09/065,103

[22] PCT Filed: Aug. 27, 1997

[86] PCT No.: PCT/EP97/04665

§ 371 Date: May 22, 1998

§ 102(e) Date: May 22, 1998

[87] PCT Pub. No.: WO98/09154

PCT Pub. Date: Mar. 5, 1998

[30] Foreign Application Priority Data

Aug. 29, 1996 [DE] Germany ............................ 196 34 873

[51] Int. Cl.[7] ............................ C12Q 1/68; G01N 33/53; C12M 1/00; G02B 21/00; B01D 59/44
[52] U.S. Cl. ............................ 435/6; 435/7.1; 435/283.2; 536/24.3; 536/24.31; 536/24.32; 359/368; 250/282; 250/458.1; 204/452
[58] Field of Search ............................ 435/6, 7.1, 283.1, 435/287.2, 286.5; 536/24.3, 24.31, 24.32; 359/368; 250/282, 458.1; 204/452

[56] References Cited

U.S. PATENT DOCUMENTS

| | | | |
|---|---|---|---|
| 4,877,965 | 10/1989 | Dandiker et al. | 250/458.1 |
| 4,923,819 | 5/1990 | Fernandez et al. | 436/518 |
| 5,039,219 | 8/1991 | James et al. | 250/458.1 |
| 5,252,834 | 10/1993 | Lin | 250/458.1 |
| 5,323,008 | 6/1994 | Studholme et al. | 250/458.1 |
| 5,418,371 | 5/1995 | Aslund et al. | 250/458.1 |
| 5,498,324 | 3/1996 | Yeung et al. | 204/452 |
| 5,674,743 | 10/1997 | Ulmer et al. | 435/287.2 |
| 5,871,906 | 2/1999 | Dyer et al. | 435/6 |

OTHER PUBLICATIONS

Bush et al Analytical Biochemistry vol. 202, pp. 146–151, 1992.

*Primary Examiner*—Kenneth R. Horlick
*Assistant Examiner*—Jeffrey Siew
*Attorney, Agent, or Firm*—Arent Fox Kintner Plotkin & Kahn, PLLC

[57] ABSTRACT

System and method for distinguishing at least two types of molecule groups that are bound to analyte molecules and which have different fluorescent characteristics. The system performs differentiation using time-resolved fluorescence measurement and includes a light source that exposes a first sample volume to light that is suitable for exciting the at least two types of molecule groups to fluorescence. The system also includes a detector for detecting fluorescence radiation emitted from a second sample volume that at least partially overlaps the first sample volume, and a control unit that is designed to activate the light source for a time interval $T_1$ and, after time interval $T_2$ has passed, to activate the detector for a time interval $T_3$. According to this system, the illumination and detection of emitted fluorescence radiation is performed at least 1,000 times per millisecond, the detector signals recorded with a recording unit during time interval $T_3$ are evaluated using an evaluation unit, and the signal over time during time interval $T_3$ is used to determine which of the at least two groups of molecules is contained in the overlapping sample volume.

55 Claims, 6 Drawing Sheets

SYSTEM FOR DISTINGUISHING FLUORESCENT MOLECULE GROUPS BY TIME RESOLVED FLUORESCENCE MEASUREMENT

FIELD OF INVENTION

The present invention concerns a system for distinguishing at least two types of groups of molecules having different fluorescent characteristics that are bound to analyte molecules. The system performs differentiation using time-resolved fluorescence measurement and includes a light source that exposes a first sample volume to light that is suitable for exciting the at least two types of molecular groups to fluorescence. The system also includes a detector for detecting fluorescence radiation emitted from a second sample volume that at least partially overlaps the first sample volume, and a control unit that is designed to activate the light source for a time interval $T_1$ and, after time interval $T_2$ has passed, to activate the detector for a time interval $T_3$. According to this system, the illumination and detection of emitted fluorescence radiation is performed at least 1,000 times per millisecond, the detector signals recorded with a recording unit during time interval $T_3$ are evaluated with an evaluation unit, and the signal behavior over time during time interval $T_3$ is used to determine which of the at least two groups of molecules is contained in the overlapping sample volume.

The present invention belongs to the field of chemical analysis based on detection of excited fluorescence radiation. Analytical methods of this nature have a very broad array of potential applications, although biochemistry has recently become one of the most significant applications. In particular, fluorescence radiation can be employed in order to sequence nucleic acids, as described in EP-B-0 157 280, for instance. This sequencing method produces cloned DNA strands which are broken down into fragments, the termini of which contain the fluorescently-labelled bases A, G, C, and T. Apparatuses are also known in the prior art that are described in U.S. Pat. No. 5,252,834, for instance, with which undesired background radiation can be blocked by properly coordinating the timing of the excitation light and the detected fluorescent light. The apparatus described in U.S. Pat. No. 5,252,834, however, is complex and utilizes spectral analysis of the emitted fluorescence radiation in order to identify analyte molecules.

In EP-A-0 563 998, a method for detecting biomolecules is described that is based on time-resolved laser spectroscopy. The method described here is based on the fact that the molecules to be detected are labelled with various fluorescent dyes that emit fluorescence for different lengths of time. The duration of the fluorescence signals are distinguished from each other by means of time-resolved fluorescence spectroscopy, and the emitted fluorescence is detected after the excitation light in order to suppress background radiation.

The methods and devices of the prior art described are based on the fact that there is a large number of molecules having the same fluorescence characteristics, which makes it possible to detect and characterize the fluorescent molecule. In order to accomplish this, the concentration of molecules must either be sufficiently high, or a sample volume of sufficient size must be exposed to light. Both of these methods, which are designed to capture fluorescent light from a large number of molecules, have a disadvantage in that the ensemble of molecules does not necessarily have to be homogeneous, i.e., molecules having different fluorescent characteristics may be detected. If the fluorescence radiation is evaluated based on the duration of the fluorescence, the ensemble of molecules under consideration will be assigned a common and, therefore, averaged, duration of fluorescence. This can result in the assignment being incorrect or the results being misinterpreted. Moreover, the methods of the state of the art have a disadvantage in that the presence of just a few molecules of one type can make it impossible to reliably assign them to a group of molecules due to statistical signal fluctuations and low signal intensities.

SUMMARY OF THE INVENTION

These disadvantages of the prior art are eliminated by a system for distinguishing different types of fluorescent groups of molecules according to the present invention. Using a system according to the present invention, the molecules under investigation can be reliably distinguished and assigned to certain groups even if the sample volume under investigation contains just a few or even individual molecules. Another advantage of the present invention is the fact that it is suitable for investigating very small sample volumes. This creates the possibility of greatly miniaturizing detection systems like those used in DNA sequencing.

Due to their simplicity and high sensitivity, fluorescent techniques are used in a broad spectrum of applications in the field of chemical analysis. The most prominent methods of fluorescence analysis are those that do not utilize the intrinsic fluorescence of the analyte molecules itself, but that where the analyte molecules are bound to suitably fluorescent molecule groups. Fluorescent techniques are therefore very important, especially in conjunction with immunological assays or nucleic acid detection, because they can utilize specific immunological affinities or selective hybridization characteristics of oligonucleotides to analyte-nucleic acids. The substances that are capable of binding specifically to analytes, such as antibodies or detection oligonucleotides, are hereafter referred to as detection molecules. They are bound directly or indirectly to fluorescent molecules groups. The fluorescent molecule groups selected can be chosen mostly independent from the analyte molecule to be detected in the specific case and from the substance capable of specific binding. Fluorescent dyes are preferably used that have favorable characteristics such as a high quantum yield, high photostability, and/or a suitable absorption range without this selection being considerably limited by the analyte molecule to be detected.

DETAILED DESCRIPTION OF THE INVENTION

Figure 1:
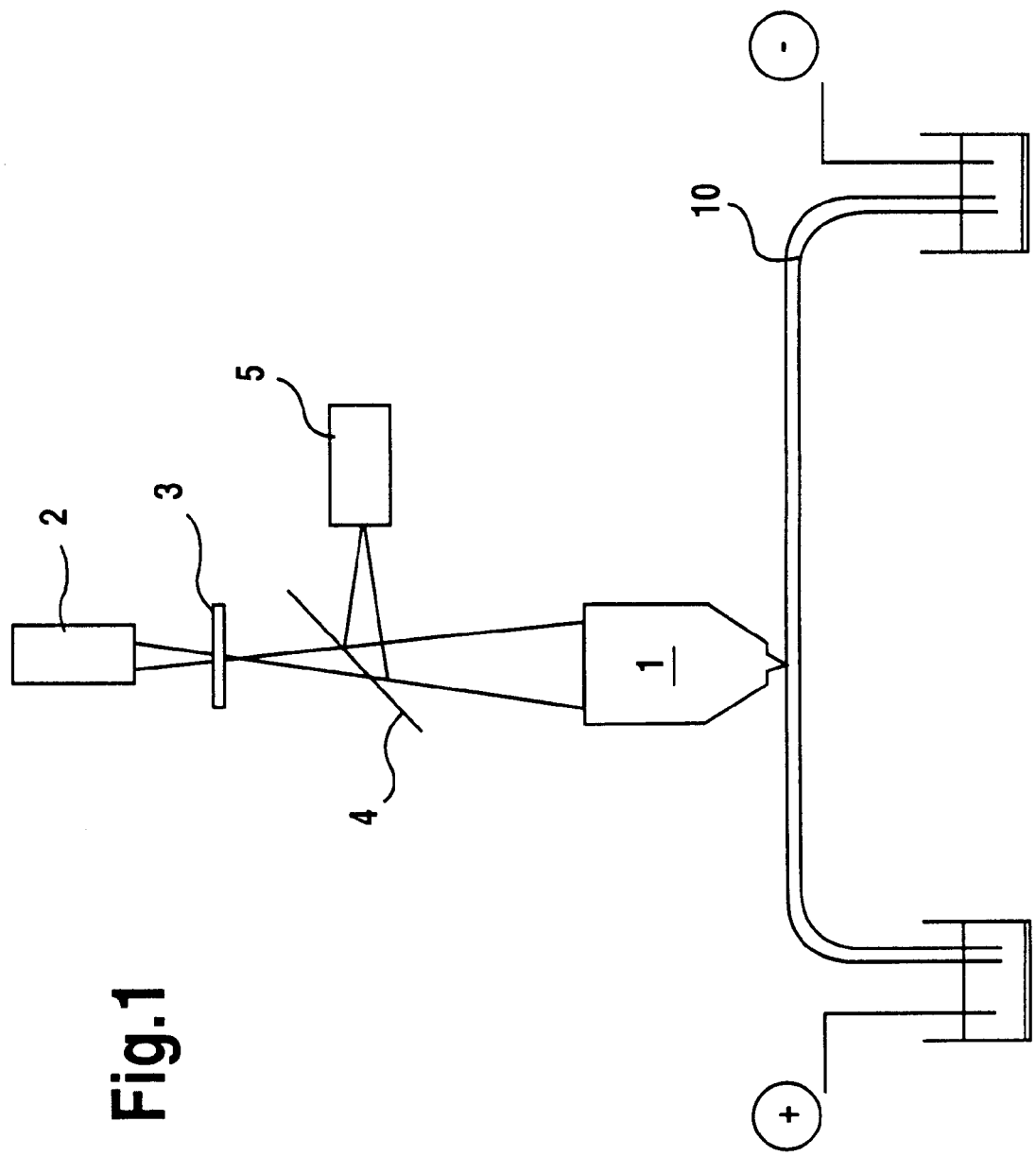
FIG. 1 shows the basis optical arrangement of a system according to the present invention.

The sensitivity of flourescent techniques is mainly limited by the background flourescence of the sample and the sample carrier. According to the present invention, the emitted fluorescent light is not detected until a predetermined length of time has passed since the fluorescence was excited. Establishing a window of time between excitation of the fluorescence and detecting the emitted fluorescence prevents the spontaneous emission of the sample or the sample container from contributing to the fluorescence signal measured. The time interval $T_2$ between exposure of the sample volume to light and activation of the detector is preferably between 0.1 and 10 ns. Another measure for increasing sensitivity according to the present invention is to expose only a small sample volume (preferably between 0.05 and 10 femtoliters) to light that is suitable for exciting fluorescent molecule groups. This can prevent fluorescence from outside the area under investigation from contributing to the signal. Traditional methods of fluorescent analysis assume that the emitted fluorescence comes from an ensemble of molecules that comprises many thousands or hundreds of thousands of molecules. On the one hand, this ensures that the signal intensity is sufficiently high, and that the durations and frequencies of fluorescence are statistically distributed. The very small sample volumes investigated according to the invention contain only very few molecules in the illuminated sample volume. However, it was found with the invention that the duration of the fluorescence of the molecules exposed to light can be statistically evaluated even though the number of molecules is small by exposing the same sample volume to light at least 1,000 times within one millisecond, and then evaluating the fluorescence radiation emitted. This finding contradicts the views in the pertinent literature. In an article entitled "Single Molecular Detection in Capillary Electrophoresis: Molecular shot noise as a fundamental limit to chemical analysis" in Analytical Chemistry, Vol. 68, pages 690–696 (1996) by D. Chen and N. J. Dovichi, it is described that an ensemble of at least $10^4$ analyte molecules must be present for fluorescence analysis to be performed, in order to decrease the imprecision caused by statistical fluctuations to less than 1%. Using the method according to the invention, however, fluorescent groups of molecules can be reliably distinguished even in an ensemble comprising fewer than $10^4$ molecules. The ensemble of molecules according to the invention preferably comprises even one or a few molecules of the same type.

The present invention can be used to advantage in the field of clinical analysis, especially in the field of immunology or nucleic acid analysis. Analyte molecules can include antigens, antibodies, nucleic acids, or fragments thereof. In general, analyte molecules can be any substance to which detection molecules can be specifically bound. On the other hand, the analyte molecules according to the invention can even contain detectable fluorescent groups of molecules themselves, or be bound to them. The latter case is common in a sequence analysis of nucleic acids. The method of sequence analysis named after Sanger is one example in this context. In this method, enzymatic synthesis is used to form the counterstrand to a nucleic acid to be sequenced. According to this method, a primer is hybridized to a single-stranded nucleic acid and elongated by inserting mononucleotides. In sequence analysis performed using Sanger's method, mononucleotide analogs are used in addition to the traditional mononucleoside triphosphates, which break the chain, i.e., the strand cannot be elongated any further after such a mononucleotide analog is inserted. In sequence analysis using fluorescence analytics, mononucleotide analogs that contain a fluorescence label are used to break the chain. Different fluorescent dyes are used to distinguish between the four possible mononucleotides. According to the invention, these fluorescent dyes are distinguished by time-resolved fluorescence measurement, which makes it possible to determine which base is at the terminus of the respective nucleic acid strand. Moreover, the present invention can be used to perform nucleic acid hybridization assays. In a preferred test format, an unlabelled capture probe—usually an oligonucleotide—is first immobilized on a surface. When incubated with a sample fluid, hybridization takes place between the capture probe and the analyte (e.g., a PCR product). If a fluorescence-labelled analyte is involved, it can be detected directly, or the analyte is then detected using a fluorescence-labelled detection probe.

The present invention can also be used to considerable advantage in the detection and differentiation of fluorescent molecules in capillaries. For instance, microcapillaries with an internal diameter of from 1 to 2 $\mu$m can be used through which the fluid to be investigated flows. An optical system is used in the investigation that detects the entire cross-section—or at least a large part thereof—of part of the microcapillary so that a fluorescent molecule can be reliably detected when it passes through the capillary. Using an arrangement like this, it is possible, for instance, to sequence individual nucleic acid strands by consecutively cleaving bases from one end of the nucleic acid strand and transporting them through the capillary in their original order. The system according to the invention can also be used in conjunction with traditional techniques such as HPLC or CGE.

Moreover, the dyes that should be distinguished from each other are distinguished according to the duration of their fluorescence. The duration of the fluorescence commonly refers to the average length of time during which an excited fluorescent dye is in the excited state. The transition from this excited state into an energetically lower state takes place spontaneously, usually within nanoseconds. Since the energetic transition of the molecule is a quantum mechanical process, the duration of the fluorescence of an individual molecule is undetermined, and the range of durations of the fluorescence observed under experimental conditions is given by the Heisenberg uncertainty principle. In order to determine the duration of the fluorescence of a type of molecule according to the prior art, an ensemble of molecules of sufficient size is exposed to light of a suitable wavelength, and a large number of molecules are excited. The transition of molecules to the final state usually takes place according to kinetics of the first order, so that an exponential decay law applies. By integrating the differential equation involved, one obtains the signal intensity as it relates to time. The duration of the fluorescence can be deduced by evaluating the course of the signal over time that is determined. If kinetics of the first order apply, this is the time after which the fluorescence intensity has decreased to 1/e. According to the invention it was found that the duration of the fluorescence can also be determined for individual molecules if a proper approach is chosen. The mean duration of the fluorescence is determined by exposing the same sample volume to light that is suitable for exciting the fluorescent group(s) of molecules at least 1,000 times within one millisecond. In evaluating the fluorescence signals determined, it is assumed that the same type of molecules are contained in the illuminated sample volume during each of the measurements. This is achieved according to the invention by investigating a small sample volume (preferably between 0.05 and 10 femtoliters) and using a suitable procedure to ensure that basically only molecules having the same duration of fluorescence are contained in the illuminated sample volume. It is also important according to the invention that the measurements in the sample volume be performed within a short period of time—preferably within fewer than 50 milliseconds—to prevent diffusion processes from having an interfering effect.

Fluorescent dyes that are suitable according to the present invention also have a sufficiently high photostability, i.e., the dyes can undergo a large number of excitation and decay cycles without decomposition. The dyes named in EP-A-0 563 998 have proven to be especially suited. Dyes from the class of rhodamine derivatives, oxazine, and carbocyanines are particularly suitable. According to the present invention it is advantageous to use at least two types of fluorescent molecules having different durations of fluorescence. This usually means that the fluorescent molecule groups as such are different. According to the invention, however, differentiations can be performed in which the fluorescent groups of molecules are identical, but in which a detectable change in the duration of the fluorescence takes place as a result of the interaction of the fluorescent molecule group and the molecule bound to it.

A system for distinguishing fluorescent dyes using time-resolved fluorescence measurement includes a light source with which a first sample volume is illuminated. Suitable light sources in particular are lasers, preferably diode lasers and flash lamps. The light sources must be sufficiently intensive and be repeatable at high frequency. The latter characteristic is given when the light source can be activated and turned off at short intervals. The repetition frequency of the light sources used is preferably greater than 10 MHz and has pulse half-widths of less than 1 nanosecond. The emission range of the light sources used is selected so that the light is sufficiently strong in the absorption range of the fluorescent dye—preferably greater than 100 mW. On the other hand, the fluorescent dyes can be selected based on a suitable absorption range if a suitable light source is already present.

Due to the main application of the system according to the invention for aqueous solutions, light sources with emission wavelengths above 600 nm are preferred. An application of the present invention in the near infrared range has proven to be particularly advantageous, because the fluorescent background radiation through the sample is low in this case, and suitable dyes are available that emit fluorescence for different lengths of time. In the especially preferred wavelength range of 630 to 670 nm, there are only very few molecules that can be excited to fluorescence, so the natural background fluorescence in this range is particularly low.

The first sample volume can be exposed to light directly from the light source, i.e., without optics situated between the two, if the light beam emitted from the light source is focused properly to ensure it hits the very small sample volume used according to the invention. However, the excitation light beam is preferably focused through a microscope optics onto an area of the sample. It is advantageous to capture the fluorescence radiation emitted by the sample with the same microscope optics and to send it to a detector. By using the same optics to output the excitation light and capture the fluorescence radiation, it can be ensured that the signals detected come from a narrowly restricted area. By using microscope optics, an aperture limits the area in the direction of the beam by the decreasing focus as the distance from the focal plane increases. In the plane vertical to the beam axis the sample area is restricted by quality of focussing and the aperture.

According to the invention, the sample is illuminated and the fluorescence radiation is detected in such a way that a first sample volume is exposed to light and the fluorescence radiation from a second sample volume that at least partially overlaps with the first sample volume is detected. An especially good overlap of illuminated and evaluated sample area can be achieved if the same optics are used to output the excitation light and capture the fluorescence radiation.

As an alternative to the embodiment described above, the sample can be exposed to light from the light source in a first direction, and, independently, the fluorescence radiation emitted can be captured in a second direction using microscope optics. These steps are preferably carried out in a 90° arrangement, i.e., the excitation and detection beams are at right angles to each other.

Fluorescence radiation emitted from the sample is directed through an optical system—preferably microscope optics—to a detector. Optical filters that filter out background radiation can also be situated in the path of the detection beam if necessary. However, one advantage of the present invention is that it does not require optical filters. When using microscope optics to capture emitted fluorescence, the beam bundle exiting the microscope optics is focused onto a detector by means of another optical system. By using this confocal arrangement, detectors with a small active surface can be used. The diameter of the detector surface is preferably less than 500 $\mu$m. Suitable detectors also have a high sensitivity to facilitate evaluation of the low intensities that occur with the arrangement selected. Semiconductor silicon detectors are especially suited due to their high quantum efficiency of up to 80% in the NIR range. If, on the other hand, photomultipliers are used that have a relatively large, active detector surface, a spacial filter (pinhole) in the beam path is used to limit the surface.

The detector is activated after the light source is activated and a waiting period $T_2$ has passed. The detector is activated for about 1 ns, and the time resolution of the signals is about 300 ps. The detector can be deactivated for a longer period of time, but should not to exceed 10 ns.

The detector signals are captured by a recording unit. A recording unit comprises a very fast converter for converting analog detector signals into digital values, which are stored. The digital values are preferably evaluated in real time, although can be evaluated delayed. A common microprocessor can be used to evaluate the digital values.

The detector signals obtained in the time interval $T_3$—after digitization and further electronic processing, if necessary—are stored in memory locations assigned to individual time intervals. A memory of this nature comprises 100 or more memory locations, for instance, that are assigned to consecutive time intervals. A time interval is preferably within the range of 0.01 to 1 nanoseconds. If a fluorescence process is detected 5 nanoseconds after the sample is exposed to light, for instance, a value will be stored in the memory location that covers a decay time of 5 nanoseconds. The value can be proportional to the signal intensity detected, although a unit value is preferably stored that shows that a fluorescence process has occurred with a duration in the duration interval indicated by the memory location. In an especially preferred application, the signal obtained by the detector can also be analyzed with regard for signal intensity, and the number of individual molecules from which the signal was emitted can be determined. The multiple of the unit value corresponding to the number of molecules in this embodiment is stored in the memory location.

The storage process described above is carried out for each measurement, and a summation is performed. This means that the unit value—or a multiple thereof, if necessary—to be stored in a certain memory location after a measurement is performed will be added to the value already present in the location. The cumulative curve that is obtained this way with the measurements for a certain sample volume can be evaluated in order to determine which fluorescent group(s) of molecules is (are) contained in the sample volume. The same evaluation methods can be used with the cumulative curve that are used for signal curves obtained with a large ensemble of molecules. By recording the absolute number of fluorescence events to precisely a few tens of picoseconds, a global analysis of photon statistics can be performed. Characteristic accumulations or pauses in the global photon distribution can be detected and determined. This makes it possible to measure the triplet life of a system and to determine the reaction kinetics. In addition, diffusion times can be measured this way via the detection volume, which can be used to deduce the size of the analyte molecule. Preferred methods for evaluating the cumulative curves obtained using the method according to the invention are described below.

Using a system according to the invention, a total collective photon efficiency of 5 to 10% can be achieved, based on the number of photons used for illumination. This results from an absorption efficiency of fluorescent dyes of approximately 80%, a probability of emission of approximately 90%, and a detector sensitivity of up to 70%. It was found that about 200 detected fluorescence events are sufficient to keep the uncertainty of the differentiation below $10^{-4}$. At concentrations of $10^{-9}$ to $10^{-12}$ mol/l, 5,000 measurements on the same sample volume are sufficient, and 10,000 are better. This indicates that a sample volume with a measurement cycle in the MHz range can be investigated according to the invention within a few milliseconds or less. It was found that the following relationship exists between concentration c[mol/l], measuring time T[s], and detection volume V[l] for a fluorescence event to occur:

$$c = l/(v \cdot T) \cdot 10^{-26} \text{ mol} \cdot s$$

Measuring time T refers to $T_3 \cdot A$, with A indicating the number of cycles in which activation and detection take place.

If the expected concentration is known, the detection volume and/or measuring time can be selected so that a number of fluorescence events is obtained that is sufficient for evaluation.

A system according to the invention also comprises a control unit that is designed to activate the light source for a time interval $T_1$ and, after a time interval $T_2$ has passed, to activate the detector for a time interval $T_3$. A control unit of this nature is suitable for facilitating time-resolved fluorescence measurement. The time interval $T_1$ at which the light source is activated is used to transfer analyte molecules in an excited state from which they change into an energetically lower state by emitting fluorescent light. The time $T_1$ is preferably in the range of 100 ps. The waiting period $T_2$ is used to exclude from the measurement any spontaneous fluorescence from the sample that is not emitted from the molecular group to be detected. The time $T_2$ preferably lies in the range between 0.1 and 10 ns. The detector is activated during time interval $T_3$ and detects fluorescence radiation emitted from the sample. The time $T_3$ is preferably selected between 20 and 100 ns. During this $T_3$ period, the signal intensity and time of occurrence of the detector signals are recorded by a recording unit. Since the measurement is performed on individual or at least a few molecules, a classic fall-off curve for fluorescence is not obtained in the time interval $T_3$. Rather, a signal peak is obtained for an individual molecule that identifies the time of occurrence and/or the time interval in which the individual molecule emits radiation. Since the measurement is repeated, a statistical evaluation can be performed from which the duration of the fluorescence lifetime can be determined. The determination of the duration of the fluorescence on one or a few molecules is problematic at first, because many molecules decompose after repeated excitation and are therefore not able to survive the number of measurement cycles required to perform an evaluation. In accordance with the present invention, fluorescent molecule groups are preferred used that survive at least 1,000 fluorescence cycles. Due to the small sample volumes used with the present invention—preferably in the range of 0.05 to 10 femtoliters—steps must be taken to ensure that the molecule or ensemble of molecules investigated do not move out of the sample volume under investigation during measurement as a result of flow or diffusion processes. The invention takes this situation into account by performing at least 1,000 measuring cycles per millisecond. Moreover, suitable statistical methods must be used to evaluate the measured results.

The maximum likelihood method and pattern recognition have proven to be especially suitable for statistical evaluation with the present invention. The signals obtained during the detection cycles $T_3$ are added up in the memory timely resolved for statistical evaluation. This means that the intensity measured in various measuring cycles at a certain time interval within $T_3$ are added up. This is performed for a sufficiently large number of different time intervals (e.g.: 1,000). The sums of intensities contained in the individual memory locations are proportional to the probability that the ensemble of molecules investigated emits fluorescence radiation within that time interval.

Using the maximum likelihood method, a duration of the fluorescence is now estimated and the probability is calculated with which the probability distribution measured under experimental conditions would have been obtained with this duration of fluorescence. The duration of the fluorescence that results in the highest probability is called the maximum likelihood estimator and is the result of the statistical evaluation. The maximum likelihood estimator is compared with the durations of the fluorescence of the different types of fluorescent molecule groups that were used in the investigation. The type of fluorescent molecular group that lies as close as possible to the maximum likelihood estimator was present in the sample volume investigated.

In the second statistical method—pattern recognition—the intensities obtained in a certain time interval within $T_3$ are added up as described earlier. Sample detection is performed with the following mathematical formula:

$$I^*(j) = \sum_{i=1}^{k} n_i \ln \frac{n_i}{p_i(j)}; \quad N = \sum_i n_i$$

In this formula, N is the sum of all photons counted over the time period $T_3$. The number of photons counted in time interval i are indicated with $n_i$. $p_i(j)$ indicates the probability that a fluorescence event will occur in the time interval i if the substance measured is of type j. The numbers of photons $n_i$ therefore represent the timely signal of the measurement performed, while $p_i(j)$ indicates the pattern of the signal for a certain substance. Using this formula, the molecule or molecules in the sample volume measured is (are) assigned to the type of fluorescent molecule group for which the value $I^*$ is smallest, taking the corresponding $p_i(j)$ as the basis.

The present invention is described in greater detail using the following figures:

FIG. 1: Optical arrangement
FIG. 2: Sample area that is evaluated
FIG. 3: Course of a measuring procedure over time
FIG. 4: Results of individual measurements
FIG. 5: Cumulative curve of individual measurements
FIG. 6: Cumulative curve from a number of individual measurements performed on a single molecule FIG. 1 shows the basic optical arrangement of a system according to the present invention. In the example shown, the sample fluid is contained in a capillary (10), part of the internal space of which is projected on a detector (2) by means of microscope optics (1). An aperture (3) is situated in front of the detector to blocks background radiation. A beam splitter (4) is situated between the microscope optics (1) and the detector (2), by means of which the light from an excitation light source (5) is coupled into the microscope optics (1). The excitation light source in the example shown is a model PLP 01 diode laser from Hamamatsu. Using this diode laser, repetition rates of 10 MHz with pulse widths of <100 psec and pulse peaks of greater than 50 mWatt can be achieved.

The fact that the excitation radiation is transmitted by the same optics with which the fluorescence radiation is captured means that a very small area of sample volume is selectively exposed to light, and the fluorescence radiation emitted from this area is evaluated. This procedure makes it possible to very precisely define the space of the sample volume investigated and prevent the measurement from being interferred with by fluorescence from outside the area investigated.

The detector (2) shown in FIG. 1 is a time-correlated single photon counter in the form of an avalance photodiode. Avalance photodiodes can be used to advantage in the field of time-resolved fluorescence spectroscopy, because they have a small detection area as compared with photomultipliers. Avalance photodiodes can therefore be used in confocal optics in particular, in which the space of the sample volume to be investigated is situated in the focal point of a first lens system, while the detection surface of the photodiode is situated in the focal point of a second lens system. With this design, only light from the desired area reaches the photodiode. This arrangement can greatly reduce the background fluorescence.

FIG. 1 also shows that the ends of the capillary (10) are in liquid contact with two reservoirs containing sample fluid. Both of the sample fluids are connected with a pole of a voltage source (not shown), so that analyte molecules can be transported electrophoretically through the capillary.

Figure 2:
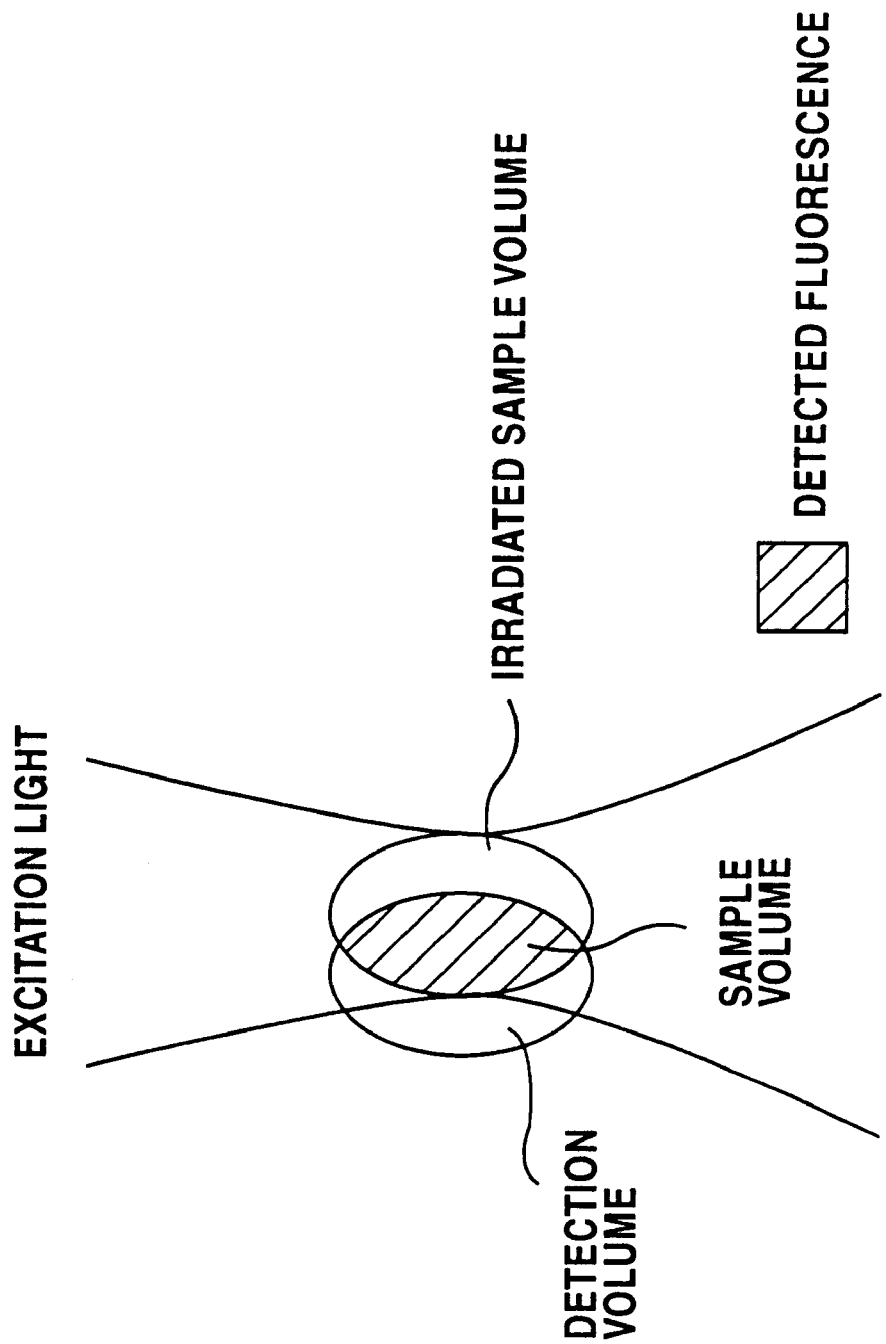
FIG. 2 depicts the sample volume that is exposed to excitation light, and the corresponding sample volume on which the detection is performed.

FIG. 2 depicts the sample volume (first sample volume) that is exposed to light from the excitation light source, and the corresponding sample volume (second sample volume) on which the detection is performed. In the ideal case, the areas shown overlap completely. In an actual case, however, the areas are shifted towards each other somewhat, so that the overlapping sample volume in which the measurement is performed is an intersection of the two volumes. The relationships shown occur when a focused excitation light beam is used and confocal detection is performed. The volume areas shown in FIG. 2 are laterally delineated by the construction of the formation lenses and aperatures, and the diode surface which acts as an aperture. The volume areas are delineated transversally by the focus range of the optics in conjunction with an aperture that excludes unfocused beams.

Figure 3:
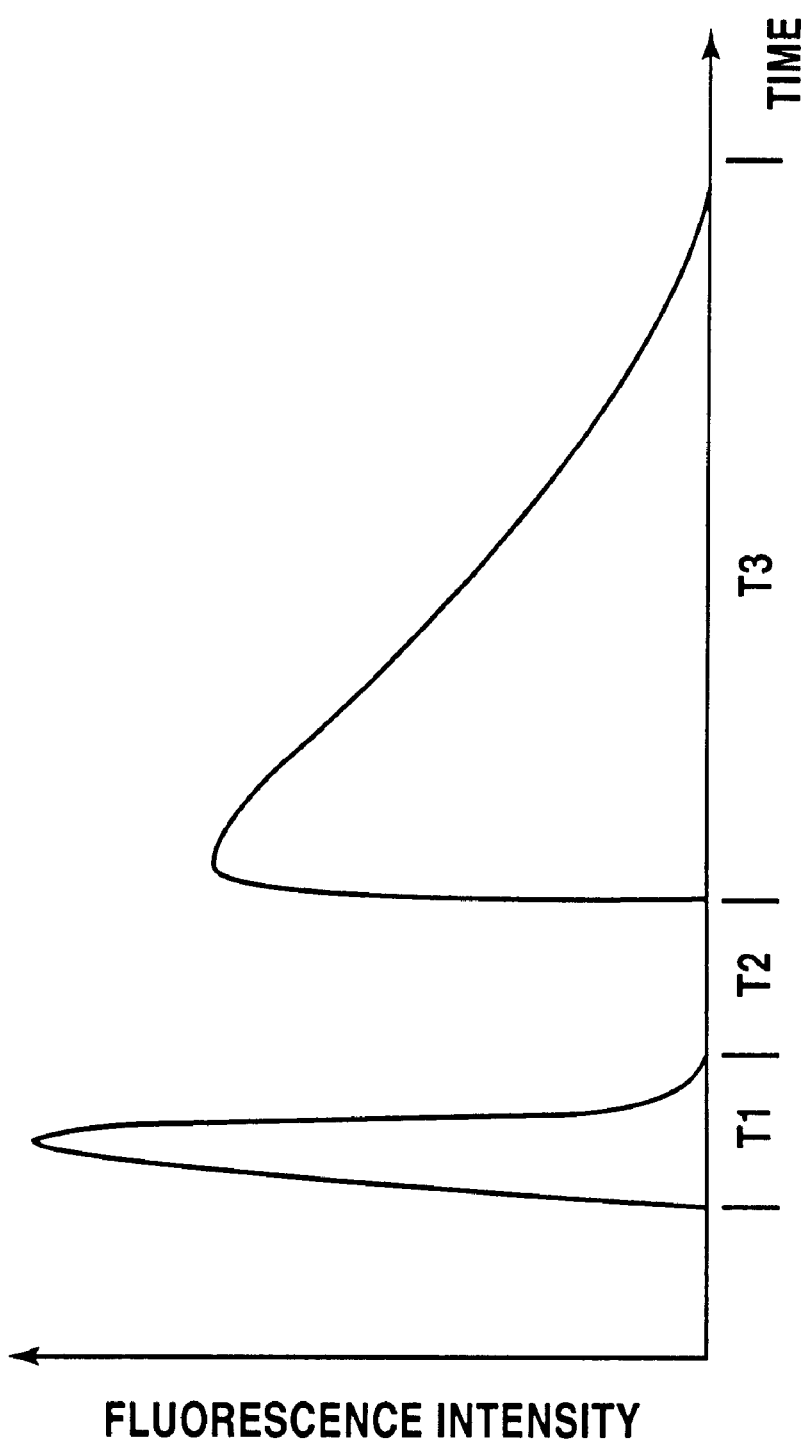
FIG. 3 shows the course of flourescence intensity over time.

FIG. 3 shows the course of fluorescence intensity over time as it can be obtained by creating a cumulative curve from many individual measurements using the method according to the invention. An excitation light impulse with a high edge steepness occurs in time interval $T_1$. With the system according to the invention, the fact that the leading edge of the excitation pulse is steep is not the only factor, but also that the light source is turned off very quickly. Particularly the time interval $T_1$ should be very small as compared with the duration of the fluorescence. The excitation light pulse is followed by time interval $T_2$ in which neither the light source nor the detector are activated, in order to exclude any spontaneous background fluorescence that occurs during this interval. The cumulative curve in time interval $T_3$ is a statistical representation of the fall-off of fluorescence emission over time. The duration of the fluorescence of the fluorescent groups of molecules can be determined from the cumulative curve.

Figure 4:
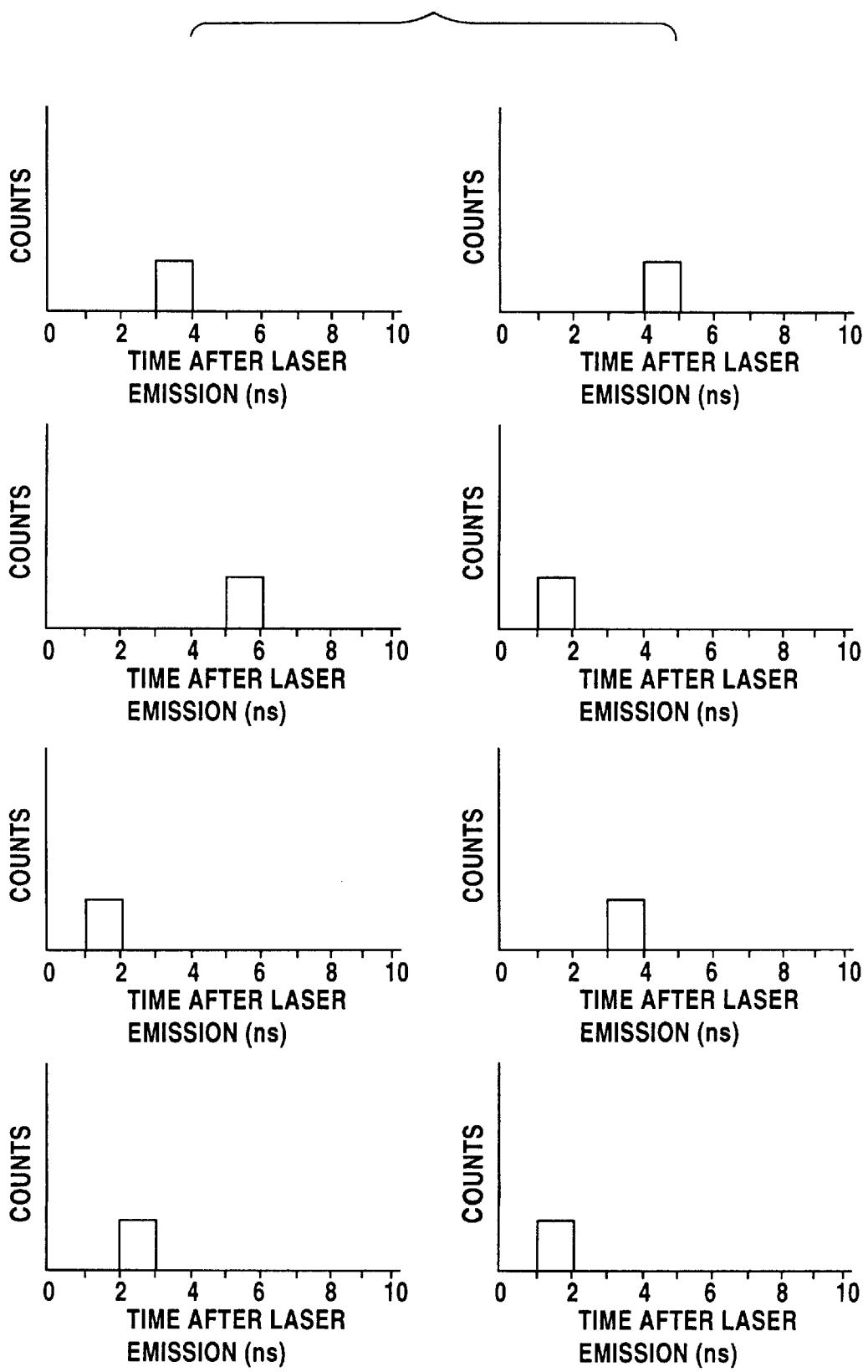
FIG. 4 shows measured results obtained form the same molecule.

FIG. 4 shows measured results obtained from the same molecule. The time that has passed since the molecule was exposed to the light source is plotted on the x-axis on each of the graphs. A unit value for a detection signal that is obtained is plotted on the y-axis. The gray-shaded box in each of the graphs indicates the time interval after which the molecule was exposed to light in which the fluorescence radiation imitated by the molecule was measured. Since the fluorescence emission is a statistical process, the fluorescence emission in the individual experiments is also detected for the same molecule after different lengths of time.

Figure 5:
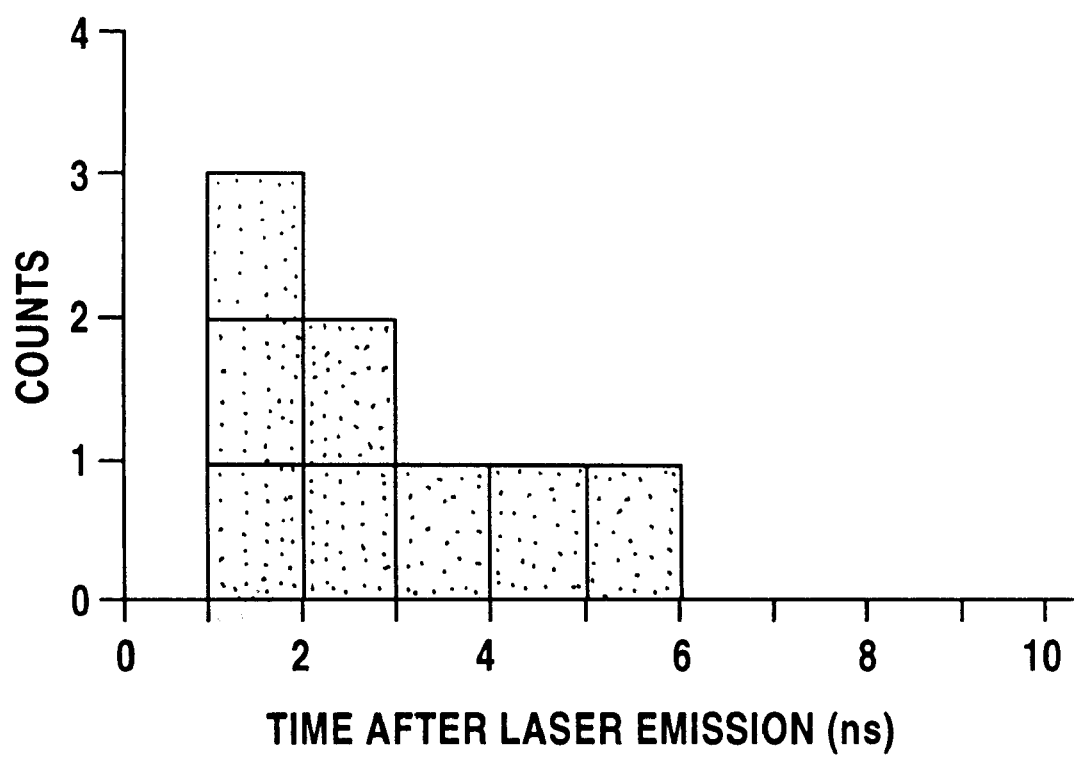
FIG. 5 shows a compilation of individual measurements from FIG 4.

FIG. 5 shows a compilation of individual measurements from FIG. 4. The unit values obtained with the individual measurements are added up for the individual periods of time. This produces a diagram that shows how often a certain range of the duration of the fluorescence was obtained with the measurements.

Figure 6:
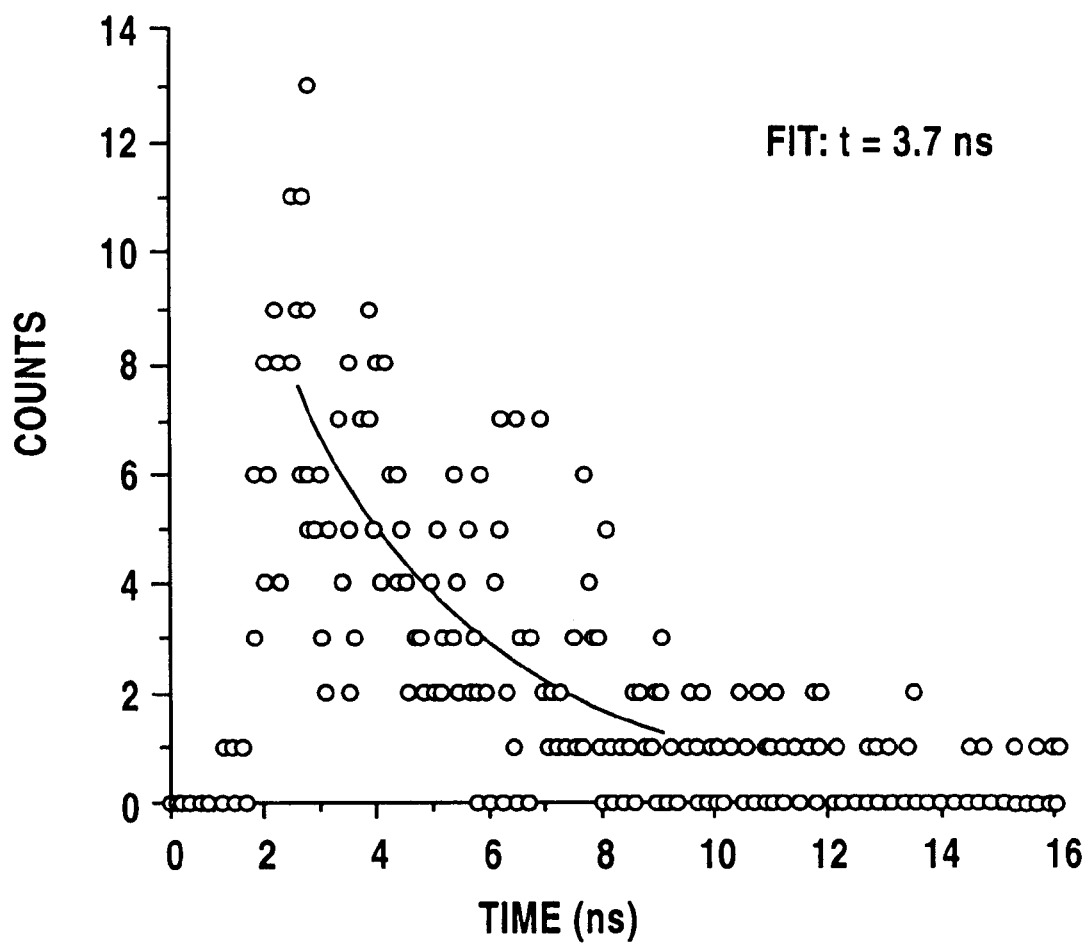
FIG. 6 shows a cummulative curve from a number of individual measurements performed on a single molecule.

FIG. 6 shows a graph corresponding to FIG. 5, but with a much higher number of individual measurements. The points shown in the figure indicate the number of times with which a certain interval of duration of the fluorescence was obtained with the measurements. The length of time between the moment the molecule was exposed to light until fluorescence radiation is emitted is plotted on the x-axis. The line drawn in the figure is a statistical representation of the fall-off of fluorescence intensity. In the actual experiment, the statistically determined duration of the fluorescence is 3.7 ns.

What is claimed is:

1. A system using time-resolved fluorescence measurement for distinguishing between at least two different types of fluorescent groups that are bound to analyte molecules in a sample, comprising (1) a light source which emits a light to illuminate a first sample volume, which light is suitable for exciting said fluorescent groups to fluorescence;

(2) a detector for detecting fluorescence radiation emitted from fluorescent groups in a second sample volume to generate signals, wherein said second sample volume at least partially overlaps with said first sample volume forming an overlapping sample volume of about 0.05 to 10 femtoliters;

(3) a control unit which performs at least 1,000 cycles per millisecond, wherein in each cycle said control unit
   (a) activates said light source for a time interval $T_1$ to illuminate said first sample volume;
   (b) waits for a time interval $T_2$; and thereafter
   (c) activates said detector for a time interval $T_3$ to detect fluorescence radiation emitted from fluorescent groups in said second sample volume generating signals;

(4) a recording unit which records the signals from said detector; and (5) an evaluation unit which uses a duration of fluorescence obtained from said signals gathered in $T_3$ over time to determine which of said at least two fluorescent groups is bound to said analyte molecules present in said overlapping sample volume.

2. The system of claim 1, wherein said at least two fluorescent groups are bound to different analyte molecules.

3. The system of claim 1, wherein said control unit performs at least 5,000 cycles per millisecond.

4. The system of claim 1, further comprising said analyte molecules, wherein said analyte molecules are present in a sample fluid at a concentration of about $10^{-9}$ to $10^{-12}$ mol/l.

5. The system of claim 1, further comprising said analyte molecules, wherein about 1 to 10 analyte molecules of the same type are contained in said first sample volume.

6. The system of claim 1, further comprising said analyte molecules, wherein said analyte molecules are nucleic acids or fragments thereof.

7. The system of claim 6, wherein said nucleic acids or fragments thereof are labelled with fluorescent dyes.

8. The system of claim 6, further comprising an unlabelled capture probe immobilized on a surface of the system.

9. The system of claim 6, wherein said nucleic acids or fragments thereof are unlabelled, said system further comprising a fluorescent-labelled detection probe.

10. The system of claim 1, further comprising said analyte molecules, wherein said analyte molecules are antigens or antibodies.

11. The system of claim 6, wherein said at least two different types of fluorescent groups are four different types of fluorescent groups, each of which is bound to a different type of nucleotide.

12. The system of claim 1, further comprising said analyte molecules having said at least two fluorescent groups bound, wherein said at least two different types of fluorescent groups are fluorescent dyes that can undergo at least 1,000 excitation and decay cycles without decomposition.

13. The system of claim 12, wherein said fluorescent dyes comprise rhodamine, oxazine or carbocyanine.

14. The system of claim 1, wherein said light source is a laser or flash lamp.

15. The system of claim 14, wherein said laser is a diode laser.

16. The system of claim 1, wherein said light source is a semiconductor laser with a wavelength in the range of about 620 nm to about 900 nm.

17. The system of claim 1, wherein said light source has a repetition frequency greater than 10 MHz and pulse half-widths of less than 1 nanosecond.

18. The system of claim 1, wherein said light source has an emission range greater than 100 mW.

19. The system of claim 1, wherein said light source has an emission wavelength above 600 nm.

20. The system of claim 19, wherein said light source has an emission wavelength of about 630–670 nm.

21. The system of claim 1, further comprising a microscope optics to focus excitation light beams from the light source onto said first sample volume.

22. The system of claim 1, wherein fluorescence radiation emitted by fluorescent groups in said second sample volume is captured by a microscope optics.

23. The system of claim 22, wherein fluorescence radiation emitted by fluorescent groups in said second sample volume is captured by said microscope optics and sent by said microscope optics to said detector.

24. The system of claim 1, wherein said microscope optics is a confocal, optical unit.

25. The system of claim 1, wherein said sample is a liquid sample situated within a cylinder, the diameter of which is less than 50 μm.

26. The system of claim 1, wherein said sample moves with a linear speed of less than 10 m/s.

27. The system of claim 1, wherein said sample is a liquid flowing through a conduit with the walls of said conduit defining the second sample volume in two spatial directions.

28. The system of claim 1, wherein $T_1$ is about 100 ps.

29. The system of claim 1, wherein $T_2$ is between about 0.1–10 ns.

30. The system of claim 1, wherein $T_3$ is between about 20–1000 ns.

31. The system of claim 1, wherein $T_3$ is between about 20–100 ns.

32. A system for distinguishing between at least two different types of analyte molecules using time-resolved fluorescence measurement, wherein said analyte molecules are bound by one type of fluorescent group which produces fluorescence of different fluorescence durations for different types of analyte molecules as a result of interaction of said analyte molecules with said fluorescent group bound thereto, said system comprising (1) a light source which emits a light to illuminate a first sample volumne to excite said fluorescent group to fluorescence;

(2) a detector which detects fluorescence radiation emitted from a second sample volume that at least partially overlaps with said first sample volume to form an overlapping sample volume of about 0.05 to 10 femtoliters;

(3) a control unit which performs at least 1,000 cycles per millisecond, wherein in each cycle said control unit
   (a) activates said light source for a time interval $T_1$ to illuminate said first sample volume;
   (b) waits for a time interval $T_2$; and thereafter
   (c) activates said detector for a time interval $T_3$ to detect fluorescence radiation emitted from the fluorescent group in said second sample volume generating signals;

(4) a recording unit which records the signals from said detector; and (5) an evaluation unit which usesa fluorescence duration obtained from said signals gathered in $T_3$ over time to determine which of said at least two different types of analyte molecules is present in said overlapping sample volume.

33. A method for distinguishing between at least two different types of fluorescent groups that are bound to analyte molecules using time-resolved fluorescence measurement, comprising the following steps:

(1) activating a light source for a time interval $T_1$ to illuminate a first sample volume exciting said fluorescent groups in said first sample volume to fluorescence;

(2) waiting for a time interval $T_2$;

(3) detecting fluorescence radiation emitted from a second sample volume in a time interval $T_3$, which second sample volume at least partially overlaps with said first sample volume to form an overlapping sample volume of about 0.05 to 10 femtoliters;

(4) repeating steps (1)–(3) for at least 1,000 cycles per millisecond, (5) recording the signals from said detector; and thereafter (6) evaluating said signals gathered in $T_3$ over time to determine which of said at least two types of fluorescent groups is present in said overlapping sample volume.

34. The method of claim 33, wherein said signals are evaluated in the time interval $T_3$.

35. The method of claim 33, wherein at least 5,000 individual fluorescent events are cummulatively recorded in one second sample volume in step (5) and evaluated in one overlapping sample volume in step (6).

36. The method of claim 35, wherein at least 10,000 individual fluorescent events are cummulatively recorded in one second sample volume in step (5) and evaluated in one overlapping sample volume in step (6).

37. The method of claim 33, wherein the detector signals recorded in the time interval $T_3$ are stored in memory locations corresponding to consecutive time intervals to determine the duration of a fluorescent event by the memory location.

38. The method of claim 37, wherein at least one unit value is stored.

39. The method of claim 38, wherein the number of unit value stored in a memory location is an indication of the number of fluorescent groups emitting fluorescence radiation in the corresponding time interval.

40. The method of claim 37, wherein said signals stored in the memory are added up in the memory to generate a cumulative curve for individual fluorescent events recorded in a second sample volume.

41. The method of claim 40, further comprising evaluating said cumulative curve statistically to determine a duration of the fluorescence and using said duration to identify the fluorescent group present in the second sample volume.

42. A method using time-resolved fluorescence measurements for distinguishing between at least two different types of fluorescent groups that are bound to antigens or antibodies in a sample, comprising the following steps:
  (1) activating a light source for a time interval $T_1$ to illuminate a first sample volume, thereby exciting said fluorescent groups in said first sample volume to fluorescence; thereafter
  (2) waiting for a time interval $T_2$; thereafter
  (3) detecting fluorescence radiation emitted from a second sample volume in a time interval $T_3$, which second sample volume at least partially overlaps with said first sample volume to form an overlapping sample volume of about 0.05 to 10 femtoliters;
  (4) repeating steps (1)–(3) at least 1,000 cycles per millisecond;
  (5) recording the signals from said detector; and thereafter
  (6) evaluating said signals gathered in $T_3$ over time to determine which of said at least two types of fluorescent groups is contained in said overlapping sample volume, wherein the type of fluorescent group determined indicates the antigens or antibodies present in said sample.

43. A method for performing nucleic acid hybridization assays of a target nucleic acid in a liquid sample, comprising the following steps
  (i) labelling said target nucleic acid with one of at least two types of fluorescent groups;
  (ii) immobilizing a capture probe which is able to hybridize to said target nucleic acid;
  (iii) incubating said capture probe with said target nucleic acid in said liquid sample to allow said capture probe to hybridize to said target nucleic acids; and thereafter
  (iv) distinguishing between said at least two different types of fluorescent groups that are bound to the target nucleic acids hybridized to said capture probe using a time-resolved fluorescence measurement procedure, which comprises the following steps:
    (1) activating a light source for a time interval $T_1$ to illuminate a first sample volume, thereby exciting said fluorescent groups in said first sample volume to fluorescence; thereafter
    (2) waiting for a time interval $T_2$; thereafter
    (3) detecting fluorescence radiation emitted from a second sample volume in a time interval $T_3$, which second sample volume at least partially overlaps with said first sample volume to form an overlapping sample volume of about 0.05 to 10 femtoliters;
    (4) repeating steps (1)–(3) at least 1,000 cycles per millisecond,
    (5) recording the signals from said detector; and thereafter
    (6) evaluating said signals gathered in $T_3$ over time to determine which of said at least two types of fluorescent groups is contained in said overlapping sample volume, wherein the type of fluorescent group determined indicates the target nucleic acid hybridized to said capture probe.

44. A method for performing nucleic acid hybridization assays of a target nucleic acid in a liquid sample, comprising the following steps
  (i) immobilizing a capture probe which is able to hybridize to said target nucleic acid;
  (ii) incubating said capture probe with said target nucleic acid in said liquid sample to allow said capture probe to hybridize to the target nucleic acid;
  (iii) incubating said capture probe with a detection probe which is labelled with one of at least two types of fluorescent group; and thereafter
  (iv) distinguishing between said at least two different types of fluorescent groups bound to said detection probe using a time-resolved fluorescence measurement procedure which comprises the following steps:
    (1) activating a light source for a time interval $T_1$ to illuminate a first sample volume, thereby exciting said fluorescent groups in said first sample volume to fluorescence;
    (2) waiting for a time interval $T_2$;
    (3) detecting fluorescence radiation emitted from a second sample volume in a time interval $T_3$, which second sample volume at least partially overlaps with said first sample volume to form an overlapping sample volume of about 0.05 to 10 femtoliters;
    (4) repeating steps (1)–(3) at least 1,000 cycles per millisecond,
    (5) recording the signals from said detector; and thereafter
    (6) evaluating said signals gathered in $T_3$ over time to determine which of said at least two types of fluorescent groups is contained in said overlapping sample volume, wherein the type of fluorescent group determined indicates the target nucleic acid hybridized to said capture probe.

45. A method for sequencing DNA, comprising the following steps
  (i) hybridizing a primer to a strand of said DNA;
  (ii) making complementary strands which are complementary to said strand of said DNA by incubating said DNA with a mixture comprising dCTP, dGTP, dTTP, dATP, ddCTP, ddGTP, ddTTP and ddATP, wherein the four dideoxymononucleotides are labelled with at least four different fluorescent groups;

(iii) separating said complementary strands;

(iv) determining which nucleobase is at the terminus of the respective complementary strand with a time resolved fluorescence measurement procedure, which comprises the following steps (1) activating a light source for a time interval $T_1$ to illuminate a first sample volume, thereby exciting said fluorescent groups in said first sample volume to fluorescence;

(2) waiting for a time interval $T_2$;

(3) detecting fluorescence radiation emitted from a second sample volume in a time interval $T_3$, which second sample volume at least partially overlaps with said first sample volume to form an overlapping sample volume of about 0.05 to 10 femtoliters;

(4) repeating steps (1)–(3) at least 1,000 cycles per millisecond, (5) recording the signals from said detector; and thereafter (6) evaluating said signals gathered in $T_3$ over time to determine which of said at least four different types of flourescent groups is contained in said overlapping sample volume, wherein the type of flourescent group determined indicates the nucleobase at the terminus of the complementary strand; and thereafter (v) using the results of step (iv) to determine the nucleotide sequence of the nucleic acid.

46. A system using time-resolved fluorescence measurement for distinguishing between at least two different types of fluorescent groups that are bound to analyte molecules in a sample, comprising (1) analyte molecules having said at least two different types of fluorescent groups bound;

(2) a light source which emits a light to illuminate a first sample volume, which light is suitable for exciting said at least two different fluorescent groups to fluorescence;

(3) a detector for detecting fluorescence radiation emitted from fluorescent groups in a second sample volume to generate signals, wherein said second sample volume at least partially overlaps with said first sample volume forming an overlapping sample volume of about 0.5 to 10 femtoliters;

(4) a control unit which performs at least 1,000 cycles per millisecond, wherein in each cycle said control unit (a) activates said light source for a time interval $T_1$ to illuminate said first sample volume;

(b) waits for a time interval $T_2$; and thereafter (c) activates said detector for a time interval $T_3$ to detect fluorescence radiation emitted from fluorescent groups in said second sample volume generating signals;

(5) a recording unit which records the signals from said detector; and (6) an evaluation unit which uses said signals gathered in $T_3$ over time to obtain a fluorescence duration, wherein said fluorescence duration indicates which of said at least two fluorescent groups is present in said overlapping sample volume.

47. The system of claim 46, wherein said control unit performs at least 5,000 cycles per millisecond.

48. The method of claim 33 applied in a hybridization assay of a nucleic acid, wherein the type of flourescent groups determined in step (6) indicates hybridization of the nucleic acid.

49. A hybridization assay of a target nucleic acid, comprising (i) incubating a nucleic acid with a capture probe for the target nucleic acid, wherein either the nucleic acid or the capture probe is labelled with a type of flourescent probe;

(ii) removing any free nucleic acid and/or free capture probe to obtain a product; and thereafter (iii) applying the method of claim 33 on the product, wherein the type of flourescent groups determined in step (6) indicates the presence of the target nucleic acid.

50. The system of claim 32, wherein said at least two fluorescent groups are bound to different analyte molecules.

51. The method of claim 33, wherein said at least two fluorescent groups are bound to different analyte molecules.

52. The method of claim 42, wherein said at least two fluorescent groups are bound to different analyte antigens or antibodies.

53. The method of claim 43, wherein said at least two fluorescent groups are bound to different nucleic acids.

54. The method of claim 45, wherein said at least four fluorescent groups are bound to different nucleobases.

55. The system of claim 46, wherein said at least two fluorescent groups are bound to different analyte molecules.

* * * * *